(12) United States Patent
Kagawa et al.

(10) Patent No.: US 8,835,696 B2
(45) Date of Patent: Sep. 16, 2014

(54) METHOD OF PREPARING FLUORINE-CONTAINING ETHER

(75) Inventors: Michiru Kagawa, Settsu (JP); Aoi Nakazono, Settsu (JP); Akiyoshi Yamauchi, Settsu (JP); Meiten Koh, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 457 days.

(21) Appl. No.: 12/999,843

(22) PCT Filed: Jun. 11, 2009

(86) PCT No.: PCT/JP2009/060694
§ 371 (c)(1),
(2), (4) Date: Dec. 17, 2010

(87) PCT Pub. No.: WO2009/154135
PCT Pub. Date: Dec. 23, 2009

(65) Prior Publication Data
US 2011/0098511 A1    Apr. 28, 2011

(30) Foreign Application Priority Data

Jun. 20, 2008    (JP) .................... 2008-161639

(51) Int. Cl.
*C07C 41/42*    (2006.01)
*C07C 41/06*    (2006.01)
*C07B 41/04*    (2006.01)

(52) U.S. Cl.
CPC ............ *C07B 41/04* (2013.01); *C07C 41/06* (2013.01)
USPC .......................................... 568/682; 568/683

(58) Field of Classification Search
CPC ........................... C07C 41/06; C07B 41/04
USPC .................................................. 568/682, 683
See application file for complete search history.

(56) References Cited

U.S. PATENT DOCUMENTS

2006/0128915 A1    6/2006    Nagai et al.
2008/0086019 A1    4/2008    Okamoto et al.

FOREIGN PATENT DOCUMENTS

| CN | 1550481 A | 12/2004 |
|---|---|---|
| CN | 1636951 A | 7/2005 |
| CN | 1832909 A | 9/2006 |
| JP | 9-263559 A | 10/1997 |
| JP | 2002-201152 A | 7/2002 |
| JP | 2004-345967 A | 12/2004 |
| JP | 2005-132826 A | 5/2005 |
| JP | 2006-256967 A | 9/2006 |
| WO | 2005/014513 A1 | 2/2005 |
| WO | 2006/123563 A1 | 11/2006 |

OTHER PUBLICATIONS

Junji Murata, et al.; "Selective Synthesis of Fluorinated Ethers By Addition Reaction Of Alcohols to Fluorinated Olefins In Water"; Green Chemistry; 2002; vol. 4; pp. 60-63.

*Primary Examiner* — Rosalynd Keys
(74) *Attorney, Agent, or Firm* — Sughrue Mion, PLLC

(57) ABSTRACT

There is provided a method of preparing a high purity fluorine-containing ether which inhibits a side reaction generating an unsaturated bond and assures low cost and simple steps. When preparing the fluorine-containing ether by allowing a fluorine-containing alkyl alcohol to react with a fluorinated olefin in the presence of a basic compound, a reaction is terminated at a stage before a conversion ratio of the fluorine-containing alkyl alcohol reaches 75%.

11 Claims, No Drawings

METHOD OF PREPARING FLUORINE-CONTAINING ETHER

TECHNICAL FIELD

The present invention relates to a method of easily preparing fluorine-containing ether at high purity.

BACKGROUND ART

An example of methods of synthesizing fluorine-containing ether includes a method in which fluorine-containing alkyl alcohol is allowed to react with fluorinated olefin in water in the presence of a basic compound such as an alkali metal compound to prepare fluorine-containing ether at yield of not less than 91% (Patent Documents 1 and 2). However, in these reactions, since a basic compound is present in a reaction system, dehydrohalogenation reaction from fluorine-containing ether as a target product inevitably simultaneously proceeds as a side reaction, and as a result, a compound having an unsaturated bond is produced as a by-product in an amount of about 0.1% by mass to about 10% by mass. Further, since a boiling point of this by-product having an unsaturated bond is close to a boiling point of a target fluorine-containing ether, there is a problem that separation by distillation is difficult.

Accordingly, in Patent Document 3, the use of a phase transfer catalyst is proposed as a method of lessening this side reaction, and fluorine-containing ether is obtained at a conversion ratio of 99.99% and at purity of 97.8%. However, in this method, cost is high since an expensive phase transfer catalyst is used.

In Patent Document 4, a reaction is carried out in the presence of a secondary alcohol or a tertiary alcohol, and fluorine-containing ether is obtained at a conversion ratio of 99.99% and at purity of 99.0%. However, in this method, cost is high since a secondary alcohol or a tertiary alcohol is used.

On the other hand, there is proposed, for example, a method of adding chlorine to a compound having an unsaturated bond to form a chlorine-adduct and then conducting separation as a method of increasing purity of fluorine-containing ether from the viewpoint of separation of this by-product having an unsaturated bond (Patent Document 5). However, in this method, since light and high temperature are needed, there is a problem that apparatus such as high pressure mercury lamp are required and the number of steps is increased.

PRIOR ART DOCUMENT

Patent Document

Patent Document 1: JP9-263559A
Patent Document 2: JP2002-201152A
Patent Document 3: JP2004-345967A
Patent Document 4: JP2005-132826A
Patent Document 5: WO2006/123563

DISCLOSURE OF INVENTION

Problem to be Solved by the Invention

It is an object of the present invention to provide a method of preparing a high purity fluorine-containing ether, which inhibits a side reaction generating an unsaturated bond and assures low cost and simple steps neither by modifying a compound having an unsaturated bond to make its separation easy nor by inhibiting a side reaction but by terminating the reaction without completing the reaction, namely by terminating the reaction at a stage of low conversion ratio.

Means to Solve the Problem

Namely, the present invention relates to a method of preparing a high purity fluorine-containing ether, wherein the method is characterized in that when preparing a fluorine-containing ether by allowing a fluorine-containing alkyl alcohol to react with a fluorinated olefin in the presence of a basic compound, a reaction is terminated at a stage before a conversion ratio of the fluorine-containing alkyl alcohol reaches 75%.

It is preferable that in the preparation method of the present invention, the preparation is carried out in water, from the viewpoint that the reaction proceeds satisfactorily and recovery of the fluorine-containing ether is easy.

The present invention also relates to a method of preparing a high purity fluorine-containing ether, comprising:
(A) a step for allowing the fluorine-containing alkyl alcohol to react with the fluorinated olefin in water in the presence of the basic compound,
(B) a step for terminating the reaction at a stage before the conversion ratio of the fluorine-containing alkyl alcohol reaches 75%, and
(C) a step for recovering an organic layer containing the produced fluorine-containing ether.

In the present invention, high purity fluorine-containing ether can be prepared continuously by the preparation method further comprising:
(D) a step for adding, to a water layer containing a produced reaction mixture, the basic compound in an amount equal to or more than the amount of consumed basic compound, and/or
(E) a step for adding, to a water layer containing a produced reaction mixture, the fluorine-containing alkyl alcohol in an amount equal to or more than the amount of consumed fluorine-containing alkyl alcohol, wherein the step (C), the step (D) and/or the step (E) are carried out in an optional order after the step (B), and then the step (A), the step (B) and the step (C) are repeated.

The preparation method may further comprise a step (F) for subjecting the organic layer containing the produced fluorine-containing ether and recovered in the recovering step (C) to distillation, thereby recovering the fluorine-containing ether.

It is preferable that the reaction is terminated at a stage where the conversion ratio of the fluorine-containing alkyl alcohol is within a range of not less than 25% and not more than 65%, from the viewpoint that the reaction time is shorter, the reaction is suitable for recycling, a side reaction does not proceed and purity of the fluorine-containing ether can be made high.

It is preferable that the fluorine-containing alkyl alcohol as a starting material is a compound represented by the formula (1):

$$RfCH_2OH \tag{1}$$

wherein Rf is a fluorine-containing alkyl group.

It is preferable that the fluorinated olefin as another starting material is a compound represented by the formula (2):

$$CF_2=CXY \tag{2}$$

wherein X and Y are the same or different and each is hydrogen atom, chlorine atom, fluorine atom or trifluoromethyl group.

It is preferable that the reaction is carried out at an absolute pressure within a range from 0.4 MPa to 1.0 MPa, from the viewpoint that a side reaction does not proceed and purity of the fluorine-containing ether can be made high.

A ratio of the basic compound to one mole of the fluorine-containing alkyl alcohol of from 0.3 to 1.0 mole is preferred from the viewpoint of good reaction speed and satisfactory selectivity of the fluorine-containing ether.

Effect of the Invention

According to the present invention, there is provided a method of preparing a high purity fluorine-containing ether, in which a side reaction generating an unsaturated bond is inhibited and low cost and simple steps are assured.

Also, the preparation method is beneficial from the viewpoint of cost and mass production because a layer of the fluorine-containing ether obtained by the reaction can be easily separated from the water layer containing unreacted starting materials and also because unreacted starting materials in the water layer can be re-used.

Since the reaction is terminated at a stage where a side reaction does not proceed, an amount of compound having an unsaturated bond, separation of which is difficult, is small, and refining is carried out by simple distillation, enabling purity of the fluorine-containing ether to be higher.

EMBODIMENT FOR CARRYING OUT THE INVENTION

The method of preparing the high purity fluorine-containing ether of the present invention is characterized in that when preparing the fluorine-containing ether by allowing the fluorine-containing alkyl alcohol to react with the fluorinated olefin in the presence of the basic compound, the reaction is terminated at a stage before the conversion ratio of the fluorine-containing alkyl alcohol reaches 75%.

In the present invention, the reaction is terminated at a stage before the conversion ratio of the fluorine-containing alkyl alcohol reaches 75%. If the conversion ratio exceeds 75%, a dehydrohalogenation reaction of the target product, namely, the fluorine-containing ether proceeds, thereby increasing a proportion of a by-product having an unsaturated bond which is difficult to be separated.

According to the present invention, when the conversion ratio is up to 75%, especially up to 70%, a proportion of the unsaturated bond-containing by-product is not more than 0.3% though it depends on kinds and amounts of starting materials and basic compound to be used. Other separable impurities (for example, potassium fluoride and potassium difluoroacetate) remains, for example, in the water layer, and purity of the fluorine-containing ether in the organic layer is not less than 99.6%, and therefore, the high purity fluorine-containing ether can be easily obtained by simple distillation.

In the present invention, a lower conversion ratio is better from the viewpoint that as the conversion ratio increases, a side reaction such as generation of an olefin to be hardly separated proceeds. On the other hand, a higher conversion ratio is better from the viewpoint of increase in yield and enhancement of a reaction speed and productivity. From these points of view, a preferred timing for terminating the reaction is when the conversion ratio of the fluorine-containing alkyl alcohol is not more than 73%, further not more than 65%, furthermore not more than 55%, especially not more than 50%, and not less than 25%, further not less than 30%, especially not less than 40%.

It is preferable that the fluorine-containing alkyl alcohol as one of the starting materials is the primary fluorine-containing alkyl alcohol represented by the formula (1):

$$RfCH_2OH \quad (1)$$

wherein Rf is a fluorine-containing alkyl group, from the viewpoint of good nucleophilic addition reaction to the fluorinated olefin.

The fluorine-containing alkyl group represented by Rf is a group subjected to substitution of at least one hydrogen atom of the alkyl group with fluorine atom. Examples of the fluorine-containing alkyl group are linear or branched fluorine-containing alkyl groups having 1 to 8 carbon atoms. The number of carbon atoms is preferably 1 to 6, more preferably 1 to 4.

Examples thereof are $CF_3-$, $CF_3CF_2-$, $CF_3(CF_2)_2-$, $CF_3(CF_2)_3-$, $CF_3(CF_2)_4-$, $CF_3(CF_2)_5-$, $CHF_2CF_2-$, $CHF_2(CF_2)_3-$, $CHF_2(CF_2)_5-$, $(CF_3)_2CF-$, $(CF_3)_2CH-$ and the like, and preferred is $CF_3-$, $CF_3CF_2-$ or $CHF_2CF_2-$.

It is preferable that the fluorinated olefin as the another starting material is the compound represented by the formula (2):

$$CF_2=CXY \quad (2)$$

wherein X and Y are the same or different and each is hydrogen atom, chlorine atom, fluorine atom or trifluoromethyl group, from the viewpoint of good reactivity.

Examples thereof are $CF_2=CF_2$, $CF_2=CHF$, $CF_2=CH_2$, $CF_2=CFCl$, $CF_2=CFCF_3$ and the like, and $CF_2=CF_2$ is preferred from the viewpoint of good reactivity.

The fluorinated olefin reacts in an amount equimolar with the fluorine-containing alkyl alcohol, but in order to control the conversion ratio of the fluorine-containing alkyl alcohol up to 75%, the amount of fluorinated olefin to be actually introduced to a reaction system is preferably not more than 1.0 mole, further preferably not more than 0.8 mole, especially preferably not more than 0.7 mole, and preferably not less than 0.3 mole, further preferably not less than 0.5 mole, to 1 mole of the fluorine-containing alkyl alcohol in consideration of its amount released as an unreacted compound after the reaction.

The basic compound used in the preparation method of the present invention acts as a catalyst, and inorganic basic compounds are preferred from the point that these compounds together with the fluorine-containing alkyl alcohol easily form alkoxide. Examples thereof are hydroxides of alkali metal such as NaOH, KOH, CsOH, LiOH, $Ca(OH)_2$, and $Ba(OH)_2$; metal fluorides such as KF, CsF and LiF; and the like. From the viewpoint of good dissociation property, hydroxides of alkali metal are more preferable. From the viewpoint of good reaction speed and satisfactory selectivity of the fluorine-containing ether, the amount of basic compound is preferably not less than 0.01 mole, further preferably not less than 0.2 mole, especially preferably not less than 0.3 mole, and preferably not more than 1.0 mole, further preferably not more than 0.8 mole based on 1 mole of the fluorine-containing alkyl alcohol. From the viewpoint of safety in consideration of abnormal temperature rise due to heat resulting from a reaction with the fluorine-containing alkyl alcohol and explosive property of the formed alkoxide, it is preferable to use the basic compound in a state of 5 to 40% by mass, preferably 15 to 25% by mass in an aqueous solution.

It is preferable that the reaction of the fluorine-containing alkyl alcohol with the fluorinated olefin is usually carried out in a solvent. Examples of the solvent are water and polar organic solvents such as diethyl ether, glymes, dioxane, tetrahydrofuran and acetonitrile. In the present invention, it is preferable to use water from the viewpoint that generation of a by-product containing an unsaturated bond is easily inhibited and separation of the target product, namely the fluorine-containing ether is simple. Water is preferably ion-exchanged water or diluted water which contains less impurity.

Since the fluorinated olefin as a starting material is gaseous at normal temperature, the reaction is carried out under normal pressure or under increased pressure. The reaction pressure in absolute pressure is preferably not less than 0.05 MPa, further preferably not less than 0.2 MPa, especially preferably not less than 0.4 MPa, and preferably not more than 1.0 MPa, further preferably not more than 0.85 MPa, especially preferably not more than 0.8 MPa, from the point that a side reaction proceeds slowly and purity of the fluorine-containing ether can be made higher. The reaction temperature is from 25° C. to 90° C., preferably from 50° C. to 85° C.

When the compounds of the formula (1) and the formula (2) are used as starting materials, the fluorine-containing ether prepared in the present invention is the fluorine-containing alkyl ether represented by the formula (3):

$$RfCH_2OCF_2CHXY \quad (3)$$

wherein Rf, X and Y are as defined above. As mentioned above, in the obtained solution of fluorine-containing alkyl ether reaction product is contained a by-product (4) which contains an unsaturated bond and is generated due to dehydrohalogenation reaction by the basic compound in the reaction system. However, its amount is extremely small according to the preparation method of the present invention.

When $CF_2=CF_2$, $CF_2=CHF$ or $CF_2=CH_2$ is used as the fluorinated olefin, examples of the by-product (4) containing an unsaturated bond are the formulas (4a) to (4d):

$$RfCH_2OCF=CF_2 \quad (4a)$$

$$RfCH_2OCF=CHF \quad (4b)$$

$$RfCH_2OCF=CH_2 \quad (4c)$$

$$RfCH_2OCF=CFCl \quad (4d)$$

wherein Rf is as defined above, and
when $CF_2=CFCF_3$ is used as the fluorinated olefin, examples of the by-product (4) containing an unsaturated bond are the formulas (4e) and (4e'):

$$RfCH_2OCF=CFCF_3 \quad (4e)$$

$$RfCH_2OCF_2CF=CF_2 \quad (4e')$$

wherein Rf is as defined above.

Since the produced fluorine-containing ether and by-product hardly exhibit solubility in water, the solution of the reaction product is separated into two layers, namely, one layer is the organic layer comprising the fluorine-containing ether and the by-product and another layer is the water layer comprising the unreacted fluorine-containing alkyl alcohol and the basic compound as the starting materials. Accordingly, the organic layer comprising the fluorine-containing ether at high purity can be easily recovered.

Namely, a preferred embodiment of the present invention is the method of preparing the high purity fluorine-containing ether, comprising:
(A) a step for allowing the fluorine-containing alkyl alcohol to react with the fluorinated olefin in water in the presence of the basic compound,
(B) a step for terminating the reaction at a stage before the conversion ratio of the fluorine-containing alkyl alcohol reaches 75%, and
(C) a step for recovering the organic layer containing the produced fluorine-containing ether.

Also, by re-using the unreacted fluorine-containing alkyl alcohol and the basic compound in the water layer, yield can be increased and the preparation of the fluorine-containing ether can be continued continuously.

Another preferred embodiment of the present invention is the method of continuously preparing the high purity fluorine-containing ether, comprising, in addition to the above-mentioned steps (A) to (C),
(D) a step for adding, to the water layer containing a produced reaction mixture, the basic compound in an amount equal to or more than the amount of consumed basic compound, and/or
(E) a step for adding, to the water layer containing a produced reaction mixture, the fluorine-containing alkyl alcohol in an amount equal to or more than the amount of consumed fluorine-containing alkyl alcohol, wherein the step (C), the step (D) and/or the step (E) are carried out in an optional order after the step (B), and then the step (A), the step (B) and the step (C) are repeated.

The preparation method may comprise a step (F) for subjecting the organic layer containing the fluorine-containing ether and recovered in the recovering step (C) to distillation, thereby recovering the fluorine-containing ether.

After terminating the reaction in the step (B), the solution of the reaction product comprises two layers, namely, one layer is an organic layer comprising the fluorine-containing ether and the by-product and another layer is a water layer comprising the unreacted fluorine-containing alkyl alcohol and the basic compound as the starting materials. The organic layer is recovered from the solution of a reaction product in the step (C). The method of recovery is not limited particularly, and the organic layer is easily separated from the water layer and recovered by usual method such as a separation method of liquids.

The recovered organic layer contains only the fluorine-containing ether and a very small amount of impurities (the unsaturated bond-containing compound as a by-product and the unreacted fluorine-containing alkyl alcohol). Accordingly, by carrying out the step (F) for subjecting the organic layer to distillation, thereby recovering the fluorine-containing ether, the high purity (for example, not less than 99.7%) fluorine-containing ether can be prepared.

The step (D) is a step for adding the basic compound to the water layer for its consumption in the reaction of the step (A), and the step (E) is a step for adding the fluorine-containing alkyl alcohol to the water layer for its consumption in the reaction of the step (A). When the amounts thereof to be added is equal to or more than those consumed in the step (A), the steps (A) to (E) can be repeated. Preferably the amount is 1.0 time, further preferably 1.05 times the amount consumed in the step (A). The steps (D) and (E) are the steps for introducing additional amount, and therefore, need not be always carried out in every preparation cycle.

The order of the steps (C), (D) and (E) is not limited particularly. Namely, these steps may be carried out in the order mentioned below.
(1) After recovering the organic layer (step (C)), the step (D) and then the step (E) are conducted.
(2) After recovering the organic layer (step (C)), the step (E) and then the step (D) are conducted.
(3) After recovering the organic layer (step (C)), the step (D) and the step (E) are conducted simultaneously.
(4) After adding the basic compound to the water layer (step (D)), the step (C) and then the step (E) are conducted.

(5) After adding the basic compound to the water layer (step (D)), the step (E) and then the step (C) are conducted.
(6) After conducting the addition of the basic compound (step (D)) and the addition of the fluorine-containing alkyl alcohol (step (E)) to the water layer simultaneously, the step (C) is conducted.
(7) After conducting the addition of the fluorine-containing alkyl alcohol to the water layer (step (E)), the step (C) and then the step (D) are conducted.
(8) After conducting the addition of the fluorine-containing alkyl alcohol to the water layer (step (E)), the step (D) and then the step (C) are conducted.

Among the above-mentioned orders, the order (4) is advantageous since the fluorine-containing alkyl alcohol contained in a trace amount in the organic layer can be completely recovered. As mentioned above, the steps (D) and (E) need not be always carried out in every preparation cycle.

When after carrying out the steps (C) to (E), fluorinated olefin is added and the step (A) and then the step (B) are conducted, it becomes possible to re-use unreacted starting materials remaining due to decrease in the conversion ratio and to increase yield.

EXAMPLE

The present invention is then explained by means of examples and comparative examples, but is not limited to these examples.

Methods of measurement employed in the present invention are as follows.
(1) NMR: AC-300 available from BRUKER is used.
$^{19}$F-NMR:
Measuring conditions: 282 MHz (trichlorofluoromethane=0 ppm)
$^{1}$H-NMR:
Measuring conditions: 300 MHz (tetramethylsilane=0 ppm)
(2) Gel chromatography (GC): GC-17A available from SHIMADZ CORPORATION is used. Column: DB624 (Length: 60, I.D: 0.32, Film: 1.8 μm)

Example 1

Step (A)

The inside of a 6-liter stainless steel autoclave was evacuated, and after introducing potassium hydroxide (546 g: 9.75 mole), water (2,184 ml) and 2,2,3,3-tetrafluoropropyl alcohol (fluorine-containing alkyl alcohol):

(1,716 g: 13 mole), evacuation and replacement with nitrogen gas of the inside of the autoclave were conducted 20 times at room temperature. After evacuation of the system, tetrafluoroethylene was introduced to give the inside pressure of the system of 0.1 MPa, and heating was conducted to give the inside temperature of 75° C. After the inside temperature had reached 75° C., tetrafluoroethylene was added little by little so as to maintain the reaction pressure at 0.7 MPa to 0.8 MPa. The inside temperature was adjusted so as to be maintained at 75° C. to 95° C.

Step (B)

When the amount of added tetrafluoroethylene reached 0.7 mole to 1 mole of fluorine-containing alkyl alcohol, supply of tetrafluoroethylene was stopped and the reaction was continued with stirring. When lowering of the inside pressure of the autoclave stopped, the inside temperature of the autoclave was brought to room temperature and unreacted tetrafluoroethylene was discharged to terminate the reaction.

In the autoclave, a solution of reaction product separated into two layers of a lower organic layer (ether layer, specific gravity: 1.6) and an upper water layer had been formed. After sampling the upper water layer, the amounts of potassium fluoride and potassium difluoroacetate which were products by the side reaction of tetrafluoroethylene and potassium hydroxide and further the amount of unreacted fluorine-containing alkyl alcohol were determined by $^{19}$F-NMR. Potassium fluoride was 3.0 mole, potassium difluoroacetate was 1.4 mole, and unreacted fluorine-containing alkyl alcohol was 7.1 mole.

Step (D)

From the amounts of potassium fluoride and potassium difluoroacetate determined above, the amount of consumed potassium hydroxide was calculated (3.0 mole+1.4 mole=4.4 mole), and a consumed amount (246 g: 4.4 mole) of potassium hydroxide was added to the water layer remaining in the solution of reaction product.

Step (C)

Then, after washing the lower organic layer in the solution of reaction product with water once, the organic layer was separated and recovered.

The amount of recovered organic layer was 1,369 g, and as a result of $^{19}$F-NMR and $^{1}$H-NMR analyses, the organic layer contained fluorine-containing ether represented by $HCF_2CF_2CH_2OCF_2CF_2H$ and its purity measured by GC was 99.72%. The amount of this produced fluorine-containing ether (1,369 g×0.9972=1,365 g: 5.9 mole) was an amount corresponding to 47.4% when converted to the conversion ratio of the fluorine-containing alkyl alcohol. At this stage, the yield was 42.3%.

Step (E)

From the amount of unreacted fluorine-containing alkyl alcohol determined above, the amount of consumed fluorine-containing alkyl alcohol was calculated (Charged fluorine-containing alkyl alcohol (13 mole)−unreacted fluorine-containing alkyl alcohol (7.1 mole)=5.9 mole), and a consumed amount (779 g: 5.9 mole) of fluorine-containing alkyl alcohol was added to the water layer remaining in the solution of reaction product.

Step (F)

1,357 g of the organic layer obtained in the step (C) was subjected to simple distillation, and fluorine-containing ether having purity (GC analysis) of 99.73% was obtained at yield of 95%. Repeating the steps after the step (A)

After completion of the step (E), the procedures of the step (A) were repeated and then the reaction was stopped under the same condition (conversion ratio: 45%) as in the step (B) and the produced organic layer was separated and recovered (step (C)). The fluorine-containing ether was recovered in an amount of 1,290 g at purity (GC analysis) of 99.76%, and further was subjected to simple distillation (step (F)). As a result, fluorine-containing ether having purity (GC analysis) of 99.77% was obtained at yield of 97.0%.

Example 2

The steps (A) to (F) were carried out in the same manner as in Example 1 except that in the step (A), the reaction pressure was changed as shown in Table 1, and in the step (B), supply of tetrafluoroethylene was stopped and the reaction was terminated when the amount of tetrafluoroethylene reached 1.0 mole to 1 mole of the fluorine-containing alkyl alcohol. The results are shown in Table 1.

Example 3

The steps (A) to (F) were carried out in the same manner as in Example 1 except that in the step (A), the reaction pressure was changed as shown in Table 1, and in the step (B), supply of tetrafluoroethylene was stopped and the reaction was terminated when the amount of tetrafluoroethylene reached 0.5 mole to 1 mole of the fluorine-containing alkyl alcohol. The results are shown in Table 1.

Example 4

The steps (A) to (F) were carried out in the same manner as in Example 1 except that in the step (A), the amount of potassium hydroxide was changed to 218 g (3.90 mole) which was 0.3 mole to 1 mole of the fluorine-containing alkyl alcohol. The results are shown in Table 1.

Example 5

The steps (A) to (F) were carried out in the same manner as in Example 1 except that in the step (A), the amount of potassium hydroxide was changed to 728 g (13.0 mole) which was 1.0 mole to 1 mole of the fluorine-containing alkyl alcohol. The results are shown in Table 1.

Example 6

The steps (A) to (F) were carried out in the same manner as in Example 1 except that in the step (A), sodium hydroxide was used instead of potassium hydroxide, its amount was changed to 390 g (9.75 mole) which was 0.75 mole to 1 mole of the fluorine-containing alkyl alcohol, and water was added (1,950 ml). The results are shown in Table 1.

Example 7

The steps (A) to (F) were carried out in the same manner as in Example 1 except that in the step (A), sodium hydroxide was used instead of potassium hydroxide, its amount was changed to 156 g (3.90 mole) which was 0.3 mole to 1 mole of the fluorine-containing alkyl alcohol, water was added (390 ml), and further in the step (B), supply of tetrafluoroethylene was stopped and the reaction was terminated when the amount of tetrafluoroethylene reached 1.0 mole to 1 mole of the fluorine-containing alkyl alcohol. The results are shown in Table 1.

Example 8

The steps (A) to (F) were carried out in the same manner as in Example 1 except that in the step (A), the reaction pressure was changed as shown in Table 1, and the amount of potassium hydroxide was changed to 400 g (7.15 mole) which was 0.55 mole to 1 mole of the fluorine-containing alkyl alcohol. The results are shown in Table 1.

Example 9

The steps (A) to (F) were carried out in the same manner as in Example 8 except that in the step (A), the amount of tetrafluoroethylene was changed to 1,100 g (11 mole) which was 0.83 mole to 1 mole of the fluorine-containing alkyl alcohol. The results are shown in Table 1.

Example 10

The steps (A) to (F) were carried out in the same manner as in Example 1 except that in the step (A), potassium fluoride was used instead of potassium hydroxide, its amount was changed to 151 g (2.60 mole) which was 0.2 mole to 1 mole of the fluorine-containing alkyl alcohol, acetonitrile (2,184 ml) was added instead of water, and further in the step (B), supply of tetrafluoroethylene was stopped and the reaction was terminated when the amount of tetrafluoroethylene reached 1.0 mole to 1 mole of the fluorine-containing alkyl alcohol. The results are shown in Table 1.

Comparative Example 1

The steps (A) to (F) were carried out in the same manner as in Example 1 except that in the step (A), the amount of potassium hydroxide was changed to 218 g (3.90 mole) which was 0.3 mole to 1 mole of the fluorine-containing alkyl alcohol, water was added (31 ml), and further in the step (B), supply of tetrafluoroethylene was stopped and the reaction was terminated when the amount of tetrafluoroethylene reached 1.0 mole to 1 mole of the fluorine-containing alkyl alcohol. The results are shown in Table 1.

Comparative Example 2

The steps (A) to (F) were carried out in the same manner as in Example 1 except that in the step (A), the amount of potassium hydroxide was changed to 218 g (3.90 mole) which was 0.3 mole to 1 mole of the fluorine-containing alkyl alcohol, water was added (105 ml), and further in the step (B), supply of tetrafluoroethylene was stopped and the reaction was terminated when the amount of tetrafluoroethylene reached 1.0 mole to 1 mole of the fluorine-containing alkyl alcohol. The results are shown in Table 1.

TABLE 1

|  | Example | | | | | |
| --- | --- | --- | --- | --- | --- | --- |
|  | 1 | 2 | 3 | 4 | 5 | 6 |
| Fluorinated olefin | | | | | | |
| Kind | TFE | TFE | TFE | TFE | TFE | TFE |
| Amount [1] | 0.7 | 1.0 | 0.5 | 0.7 | 0.7 | 0.7 |

TABLE 1-continued

| Basic compound | | | | | | |
|---|---|---|---|---|---|---|
| Kind | KOH | KOH | KOH | KOH | KOH | NaOH |
| Amount [1] | 0.75 | 0.75 | 0.75 | 0.3 | 1.0 | 0.75 |
| Concentration (% by mass) [2] | 20 | 20 | 20 | 20 | 20 | 20 |
| Solvent | | | | | | |
| Kind | water | water | water | water | water | water |
| Reaction temperature (° C.) | 75 to 95 | 75 to 95 | 75 to 95 | 75 to 95 | 75 to 95 | 75 to 95 |
| Reaction time (hr) | 5.0 | 10.1 | 3.3 | 5.0 | 5.0 | 5.0 |
| Reaction pressure (MPa) | 0.7 to 0.8 | 0.65 to 0.7 | 0.5 to 0.8 | 0.7 to 0.8 | 0.7 to 0.8 | 0.7 to 0.8 |
| Conversion ratio (%) | 47.4 | 61.8 | 28.7 | 43.9 | 48.8 | 40.4 |
| Fluorine-containing ether Purity (%) | | | | | | |
| after the step (C.) | 99.72 | 99.77 | 99.70 | 99.88 | 99.68 | 99.83 |
| after the step (F.) | 99.73 | 99.8 | 99.72 | 99.88 | 99.7 | 99.83 |
| Yield (%) | | | | | | |
| after the step (C.) | 42.3 | 61.8 | 28.7 | 43.9 | 43.7 | 40.3 |
| after the step (F.) | 95.0 | 94.0 | 98.0 | 97.5 | 98.0 | 98.5 |

| | Example | | | | Com. Ex. | |
|---|---|---|---|---|---|---|
| | 7 | 8 | 9 | 10 | 1 | 2 |
| Fluorinated olefin | | | | | | |
| Kind | TFE | TFE | TFE | TFE | TFE | TFE |
| Amount [1] | 1.0 | 0.7 | 0.83 | 1.0 | 1.0 | 1.0 |
| Basic compound | | | | | | |
| Kind | NaOH | KOH | KOH | KF | KOH | KOH |
| Amount [1] | 0.3 | 0.55 | 0.55 | 0.2 | 0.3 | 0.3 |
| Concentration (% by mass) [2] | 40 | 20 | 20 | — | 20 | 20 |
| Solvent | | | | | | |
| Kind | water | water | water | $CH_3CN$ | water | water |
| Reaction temperature (° C.) | 75 to 95 | 75 to 95 | 75 to 95 | 75 to 95 | 75 to 95 | 75 to 95 |
| Reaction time (hr) | 13.6 | 8.5 | 9.0 | 4.3 | 15.0 | 17.0 |
| Reaction pressure (MPa) | 0.7 to 0.8 | 0.75 to 0.8 | 0.75 to 0.8 | 0.7 to 0.8 | 0.7 to 0.8 | 0.7 to 0.8 |
| Conversion ratio (%) | 57.5 | 62.7 | 73 | 25.0 | 78 | 85.3 |
| Fluorine-containing ether Purity (%) | | | | | | |
| after the step (C.) | 99.83 | 99.73 | 99.76 | 99.70 | 98.17 | 99.21 |
| after the step (F.) | 99.83 | 99.77 | 99.77 | 99.71 | 98.25 | 99.31 |
| Yield (%) | | | | | | |
| after the step (C.) | 57.4 | 62.7 | 72 | 24.3 | 43.7 | 40.3 |
| after the step (F.) | 98.5 | 98.5 | 98.5 | 94.0 | 97.0 | 96.5 |

[1]: Mole to 1 mole of fluorine-containing alkyl alcohol
[2]: Concentration of aqueous solution of basic compound From Table 1, it is seen that when the conversion ratio of alcohol is between 28% and 73%, purity of fluorine-containing ether is not less than 99.7%, any of KOH, NaOH and KF can be used as a basic compound, and even a polar organic solvent other than water is effective as a solvent. The results of Comparative Examples 1 and 2 indicate that when the conversion ratio exceeds 75%, selectivity becomes inferior, longer reaction time is required, and reaction is inefficient.

Also from the viewpoint of recycling, it can be said that the conversion ratio of the fluorine-containing alkyl alcohol of 40 to 73% is especially suitable in view of yield and reaction time.

Example 11

Step (A)

The inside of a 3-liter stainless steel autoclave was evacuated, and after introducing potassium hydroxide (85 g: 1.5 mole), water (800 ml) and 2,2,3,3-tetrafluoropropyl alcohol (fluorine-containing alkyl alcohol):

$HCF_2CF_2CH_2OH$ (600 g: 4.5 mole), evacuation and replacement with nitrogen gas of the inside of the autoclave were conducted three times at room temperature. After evacuation of the system, hexafluoropropylene ($CF_2$=$CFCF_3$) was introduced to give the inside pressure of the system of 0.1 MPa, and heating was conducted to give the inside temperature of 50° C. After the inside temperature had reached 50° C., hexafluoropropylene was added little by little so as to maintain the reaction pressure at 0.4 MPa to 0.5 MPa. The inside temperature of the system was adjusted so as to be maintained at 50° C. to 60° C.

Step (B)

When the amount of added hexafluoropropylene reached 0.6 mole to 1 mole of fluorine-containing alkyl alcohol, supply of hexafluoropropylene was stopped and the reaction was continued with stirring. When lowering of the inside pressure of the autoclave stopped, the inside temperature of the autoclave was brought to room temperature and unreacted hexafluoropropylene was discharged to terminate the reaction.

In the autoclave, a solution of reaction product separated into two layers of a lower organic layer (ether layer) and an upper water layer had been formed. After sampling the upper water layer, the amount of unreacted fluorine-containing alkyl alcohol determined by $^{19}$F-NMR was 7.1 mole. Whether or not impurities were present was checked, and neither potassium fluoride nor potassium difluoroacetate was detected.

Step (C)

Then, after washing the lower organic layer in the solution of reaction product with water once, the organic layer was separated and recovered.

The amount of recovered organic layer was 761 g, and as a result of $^{19}$F-NMR and $^{1}$H-NMR analyses after washing with water once, the organic layer contained fluorine-containing ether represented by:

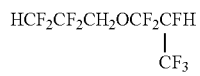

and its purity measured by GC was 99.83%. The amount of this produced fluorine-containing ether (761 g×0.9983=760 g: 2.69 mole) was an amount corresponding to 60% when converted to the conversion ratio of the fluorine-containing alkyl alcohol. At this stage, the yield was 59.8%.

Step (D)

Potassium hydroxide (basic compound) was not charged additionally.

Step (E)

From the amount of unreacted fluorine-containing alkyl alcohol determined above, the amount of consumed fluorine-containing alkyl alcohol was calculated (Charged fluorine-containing alkyl alcohol (4.5 mole)−unreacted fluorine-containing alkyl alcohol (1.85 mole)=2.65 mole), and a consumed amount (245 g: 1.85 mole) of fluorine-containing alkyl alcohol was added to the water layer remaining in the solution of reaction product.

Step (F)

761 g of the organic layer obtained in the step (C) was subjected to simple distillation, and fluorine-containing ether having purity (GC analysis) of 99.85% was obtained at yield of 99.8%.

Example 12

Step (A)

The inside of a 3-liter stainless steel autoclave was evacuated, and after introducing potassium hydroxide (101 g: 1.8 mole), water (410 ml) and 2,2,3,3,3-pentafluoropropyl alcohol (fluorine-containing alkyl alcohol):

(900 g: 6.0 mole), evacuation and replacement with nitrogen gas of the inside of the autoclave were conducted 20 times at room temperature. After evacuation of the system, tetrafluoroethylene was introduced to give the inside pressure of the system of 0.1 MPa, and heating was conducted to give the inside temperature of 75° C. After the inside temperature had reached 75° C., tetrafluoroethylene was added little by little so as to maintain the reaction pressure at 0.7 MPa to 0.8 MPa. The inside temperature of the system was adjusted so as to be maintained at 75° C. to 85° C.

Step (B)

When the amount of added tetrafluoroethylene reached 0.6 mole to 1 mole of fluorine-containing alkyl alcohol, supply of tetrafluoroethylene was stopped and the reaction was continued with stirring. When lowering of the inside pressure of the autoclave stopped, the inside temperature of the autoclave was brought to room temperature and unreacted tetrafluoroethylene was discharged to terminate the reaction.

In the autoclave, a solution of reaction product separated into two layers of a lower organic layer (ether layer) and an upper water layer had been formed. After sampling the upper water layer, the amounts of potassium fluoride and potassium difluoroacetate which were products by the side reaction of tetrafluoroethylene and potassium hydroxide and further the amount of unreacted fluorine-containing alkyl alcohol were determined by $^{19}$F-NMR. Potassium fluoride was 1.84 mole, potassium difluoroacetate was 0.86 mole, and unreacted fluorine-containing alkyl alcohol was 2.55 mole.

Step (C)

Then, the lower organic layer in the solution of reaction product was separated and recovered.

The amount of recovered organic layer was 570 g, and as a result of $^{19}$F-NMR and $^{1}$H-NMR analyses, the organic layer contained fluorine-containing ether represented by $CF_3CF_2CH_2OCF_2CF_2H$ and its purity measured by GC was 99.91%. The amount of this produced fluorine-containing ether (570 g×0.9991=569 g: 2.27 mole) was an amount corresponding to 38% when converted to the conversion ratio of the fluorine-containing alkyl alcohol. At this stage, the yield was 37.8%.

Step (D)

From the amounts of potassium fluoride and potassium difluoroacetate determined above, the amount of consumed potassium hydroxide was calculated (1.84 mole+0.86 mole=2.7 mole), and a consumed amount (151 g: 2.7 mole) of potassium hydroxide was added to the water layer remaining in the solution of reaction product.

Step (E)

From the amount of unreacted fluorine-containing alkyl alcohol determined above, the amount of consumed fluorine-containing alkyl alcohol was calculated (Charged fluorine-containing alkyl alcohol (6.0 mole)−unreacted fluorine-containing alkyl alcohol (3.72 mole)=2.28 mole), and a consumed amount (342 g: 2.28 mole) of fluorine-containing alkyl alcohol was added to the water layer remaining in the solution of reaction product.

Step (F)

570 g of the organic layer obtained in the step (C) was subjected to simple distillation, and fluorine-containing ether having purity (GC analysis) of 99.91% was obtained at yield of 99.8%.

Example 13

Step (A)

The inside of a 3-liter stainless steel autoclave was evacuated, and after introducing potassium hydroxide (240 g: 4.26 mole), water (960 ml) and 2,2,3,3-tetrafluoropropyl alcohol (fluorine-containing alkyl alcohol):

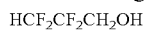
$HCF_2CF_2CH_2OH$ (750 g: 5.7 mole), evacuation and replacement with nitrogen gas of the inside of the autoclave were conducted 20 times at room temperature. After evacuation of the system, chlorotrifluoroethylene ($CF_2$=$CFCl$) was introduced to give the inside pressure of the system of 0.1 MPa, and heating was conducted to give the inside temperature of 75° C. After the inside temperature had reached 75° C., chlorotrifluoroethylene was added little by little so as to maintain the reaction pressure at 0.4 MPa (vapor pressure of chlorotrifluoroethylene). The inside temperature of the system was adjusted so as to be maintained at 75° C. to 85° C.

Step (B)

When the amount of added chlorotrifluoroethylene reached 0.6 mole to 1 mole of fluorine-containing alkyl alcohol, supply of chlorotrifluoroethylene was stopped and the reaction was continued with stirring. When lowering of the inside pressure of the autoclave stopped, the inside temperature of the autoclave was brought to room temperature and unreacted chlorotrifluoroethylene was discharged to terminate the reaction.

In the autoclave, a solution of reaction product separated into two layers of a lower organic layer (ether layer) and an upper water layer had been formed. After sampling the upper water layer, the amounts of potassium fluoride and potassium difluoroacetate which were products by the side reaction of chlorotrifluoroethylene and potassium hydroxide and further the amount of unreacted fluorine-containing alkyl alcohol were determined by $^{19}F$-NMR. Potassium fluoride was 1.30 mole, potassium difluoroacetate was 0.61 mole, and unreacted fluorine-containing alkyl alcohol was 3.11 mole.

Step (C)

Then, the lower organic layer in the solution of reaction product was separated and recovered.

The amount of recovered organic layer was 638 g, and as a result of $^{19}F$-NMR and $^1H$-NMR analyses, the organic layer contained fluorine-containing ether represented by $HCF_2CF_2CH_2OCF_2CFClH$ and its purity measured by GC was 99.85%. The amount of this produced fluorine-containing ether (638 g×0.9985=637 g: 2.56 mole) was an amount corresponding to 45.2% when converted to the conversion ratio of the fluorine-containing alkyl alcohol. At this stage, the yield was 45.1%.

Step (D)

From the amounts of potassium fluoride and potassium difluoroacetate determined above, the amount of consumed potassium hydroxide was calculated (1.30 mole+0.61 mole=1.91 mole), and a consumed amount (107 g: 1.91 mole) of potassium hydroxide was added to the water layer remaining in the solution of reaction product.

Step (E)

From the amount of unreacted fluorine-containing alkyl alcohol determined above, the amount of consumed fluorine-containing alkyl alcohol was calculated (Charged fluorine-containing alkyl alcohol (5.68 mole)–unreacted fluorine-containing alkyl alcohol (3.11 mole)=2.57 mole), and a consumed amount (340 g: 2.57 mole) of fluorine-containing alkyl alcohol was added to the water layer remaining in the solution of reaction product.

Step (F)

638 g of the organic layer obtained in the step (C) was subjected to simple distillation, and fluorine-containing ether having purity (GC analysis) of 99.91% was obtained at yield of 98.0%.

Example 14

Step (A)

The inside of a 100 ml stainless steel autoclave was evacuated, and after introducing potassium hydroxide (6.4 g: 0.12 mole), water (25 ml) and 2,2,3,3-tetrafluoropropyl alcohol (fluorine-containing alkyl alcohol):

$HCF_2CF_2CH_2OH$ (20 g: 0.15 mole), evacuation and replacement with nitrogen gas of the inside of the autoclave were conducted three times at room temperature. After evacuation of the system, vinylidene fluoride ($CF_2$=$CH_2$) was introduced to give the inside pressure of the system of 0.1 MPa, and heating was conducted to give the inside temperature of 80° C. After the inside temperature had reached 80° C., vinylidene fluoride was added little by little so as to maintain the reaction pressure at 0.8 MPa. The inside temperature of the system was adjusted so as to be maintained at 75° C. to 80° C.

Step (B)

When the amount of added vinylidene fluoride reached 0.6 mole (5.8 g) to 1 mole of fluorine-containing alkyl alcohol, supply of vinylidene fluoride was stopped and the reaction was continued with stirring. When lowering of the inside pressure of the autoclave stopped, the inside temperature of the autoclave was brought to room temperature and unreacted vinylidene fluoride was discharged to terminate the reaction.

In the autoclave, a solution of reaction product separated into two layers of a lower organic layer (ether layer) and an upper water layer had been formed. After sampling the upper water layer, the amounts of potassium fluoride and potassium difluoroacetate which were products by the side reaction of vinylidene fluoride and potassium hydroxide and further the amount of unreacted fluorine-containing alkyl alcohol were determined by $^{19}F$-NMR. Neither potassium fluoride nor potassium difluoroacetate was detected, and unreacted fluorine-containing alkyl alcohol was 0.10 mole.

Step (C)

Then, the lower organic layer in the solution of reaction product was separated and recovered.

The amount of recovered organic layer was 9.8 g, and as a result of $^{19}F$-NMR and $^1H$-NMR analyses, the organic layer contained fluorine-containing ether represented by $HCF_2CF_2CH_2OCF_2CH_3$ and its purity measured by GC was 99.85%. The amount of this produced fluorine-containing ether (9.8 g×0.9985=9.78 g: 0.05 mole) was an amount corresponding to 30% when converted to the conversion ratio of the fluorine-containing alkyl alcohol. At this stage, the yield was 30%.

Step (D)

Potassium hydroxide was not charged additionally.

Step (E)

From the amount of unreacted fluorine-containing alkyl alcohol determined above, the amount of consumed fluorine-containing alkyl alcohol was calculated (Charged fluorine-containing alkyl alcohol (0.15 mole)–unreacted fluorine-containing alkyl alcohol (0.10 mole)=0.05 mole), and a consumed amount (6.6 g: 0.05 mole) of fluorine-containing alkyl alcohol was added to the water layer remaining in the solution of reaction product.

Step (F)

9.8 g of the organic layer obtained in the step (C) was subjected to simple distillation, and fluorine-containing ether having purity (GC analysis) of 99.93% was obtained at yield of 99.8%.

The invention claimed is:

1. A method of preparing a high purity fluorine-containing ether, wherein when preparing a fluorine-containing ether by allowing a fluorine-containing alkyl alcohol to react with a fluorinated olefin in the presence of a basic compound, a reaction is terminated at a stage before a conversion ratio of the fluorine-containing alkyl alcohol reaches 75%.

2. The preparation method of claim 1, wherein the preparation is carried out in water.

3. The preparation method of claim 2, comprising:
   (A) a step for allowing the fluorine-containing alkyl alcohol to react with the fluorinated olefin in water in the presence of the basic compound,
   (B) a step for terminating the reaction at a stage before the conversion ratio of the fluorine-containing alkyl alcohol reaches 75%, and
   (C) a step for recovering an organic layer containing the produced fluorine-containing ether.

4. The preparation method of claim 3, comprising:
   (D) a step for adding, to a water layer containing a produced reaction mixture, the basic compound in an amount equal to or more than the amount of consumed basic compound, and/or
   (E) a step for adding, to a water layer containing a produced reaction mixture, the fluorine-containing alkyl alcohol in an amount equal to or more than the amount of consumed fluorine-containing alkyl alcohol, wherein the step (C), the step (D) and/or the step (E) are carried out in an optional order after the step (B), and then the step (A), the step (B) and the step (C) are repeated.

5. The preparation method of claim 3, further comprising a step (F) for subjecting the organic layer containing the produced fluorine-containing ether and recovered in the recovering step (C) to distillation, thereby recovering the fluorine-containing ether.

6. The preparation method of claim 1, wherein the reaction is terminated at a stage where the conversion ratio of the fluorine-containing alkyl alcohol is within a range of not less than 25% and not more than 65%.

7. The preparation method of claim 1, wherein the fluorine-containing alkyl alcohol is a compound represented by the formula (1):

$$RfCH_2OH \tag{1}$$

wherein Rf is a fluorine-containing alkyl group.

8. The preparation method of claim 1, wherein the fluorinated olefin is a compound represented by the formula (2):

$$CF_2{=}CXY \tag{2}$$

wherein X and Y are the same or different and each is hydrogen atom, chlorine atom, fluorine atom or trifluoromethyl group.

9. The preparation method of claim 1, wherein the reaction is carried out at an absolute pressure within a range from 0.4 MPa to 1.0 MPa.

10. The preparation method of claim 1, wherein a ratio of the basic compound to one mole of the fluorine-containing alkyl alcohol is from 0.3 mole to 1.0 mole.

11. The preparation method of claim 4, comprising (F) a step for subjecting the organic layer containing the produced fluorine-containing ether having been recovered in the recovering step (C) to distillation, thereby recovering the fluorine-containing ether.

* * * * *